(12) United States Patent
Wells et al.

(10) Patent No.: US 9,883,942 B2
(45) Date of Patent: Feb. 6, 2018

(54) TRANSAPICAL INTRODUCER

(71) Applicant: St. Jude Medical, Cardiology Division, Inc., St. Paul, MN (US)

(72) Inventors: Brian K. Wells, La Grange, KY (US); John Miser, Crestwood, KY (US); Gregory R. Furnish, Louisville, KY (US); Tracee Eidenschink, Wayzata, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 117 days.

(21) Appl. No.: 14/899,491

(22) PCT Filed: Jun. 16, 2014

(86) PCT No.: PCT/US2014/042494
§ 371 (c)(1),
(2) Date: Dec. 17, 2015

(87) PCT Pub. No.: WO2014/204840
PCT Pub. Date: Dec. 24, 2014

(65) Prior Publication Data
US 2016/0158005 A1 Jun. 9, 2016

Related U.S. Application Data

(60) Provisional application No. 61/836,440, filed on Jun. 18, 2013.

(51) Int. Cl.
*A61B 17/34* (2006.01)
*A61F 2/24* (2006.01)
*A61B 17/00* (2006.01)

(52) U.S. Cl.
CPC ........ *A61F 2/2427* (2013.01); *A61B 17/3417* (2013.01); *A61B 17/3462* (2013.01);
(Continued)

(58) Field of Classification Search
CPC . A61B 17/3498; A61B 17/34; A61B 17/3423; A61B 17/3417; A61B 1/3132;
(Continued)

(56) References Cited

U.S. PATENT DOCUMENTS

| 3,657,744 A | 4/1972 | Ersek |
| 4,423,730 A | 1/1984 | Gabbay |

(Continued)

FOREIGN PATENT DOCUMENTS

| EP | 1129744 A1 | 9/2001 |
| EP | 1157673 A2 | 11/2001 |

(Continued)

OTHER PUBLICATIONS

International Search Report for Application No. PCT/US2014/042494 dated Oct. 16, 2014.
(Continued)

*Primary Examiner* — Gerald Landry, II
(74) *Attorney, Agent, or Firm* — Lerner, David, Littenberg, Krumholz & Mentlik, LLP

(57) ABSTRACT

A transapical introducer (100) includes a housing (140) near a proximal end of the introducer, a first valve (160) in the housing, a proximal tube (130) coupled to the housing, and a distal tube (110) coupled to a distal end of the proximal tube.

13 Claims, 14 Drawing Sheets

(52) U.S. Cl.
CPC ..... *A61B 17/3498* (2013.01); *A61B 2017/00247* (2013.01); *A61B 2017/00907* (2013.01); *A61B 2017/3441* (2013.01); *A61B 2017/3488* (2013.01)

(58) Field of Classification Search
CPC .......... A61M 39/06; A61M 2039/0626; A61M 2039/064; A61M 2039/0686; A61M 2039/0646; A61M 2039/0666
USPC .... 604/158, 164.01, 167.01, 167.03, 167.04, 604/167.05, 167.06, 256, 264; 600/139
See application file for complete search history.

(56) References Cited

U.S. PATENT DOCUMENTS

| | | | |
|---|---|---|---|
| 5,613,954 A * | 3/1997 | Nelson | A61B 17/3421 604/167.03 |
| 5,843,167 A | 12/1998 | Dwyer et al. | |
| 5,924,424 A | 7/1999 | Stevens et al. | |
| 5,968,068 A | 10/1999 | Dehdashtian et al. | |
| 6,077,297 A | 6/2000 | Robinson et al. | |
| 6,306,141 B1 | 10/2001 | Jervis | |
| 6,623,518 B2 | 9/2003 | Thompson et al. | |
| 6,767,340 B2 * | 7/2004 | Willis | A61J 15/0042 604/167.03 |
| 6,814,746 B2 | 11/2004 | Thompson et al. | |
| 6,830,584 B1 | 12/2004 | Seguin | |
| 6,951,555 B1 * | 10/2005 | Suresh | A61M 25/0023 604/524 |
| 7,018,406 B2 | 3/2006 | Seguin et al. | |
| 7,311,730 B2 | 12/2007 | Gabbay | |
| 7,510,572 B2 | 3/2009 | Gabbay | |
| 7,682,390 B2 | 3/2010 | Seguin | |
| 7,727,255 B2 * | 6/2010 | Taylor | A61B 17/3423 604/167.01 |
| 7,803,185 B2 | 9/2010 | Gabbay | |
| 8,337,394 B2 * | 12/2012 | Vakharia | A61B 1/00135 600/114 |
| 8,491,533 B2 * | 7/2013 | Parihar | A61B 17/34 604/167.03 |
| 2003/0050694 A1 | 3/2003 | Yang et al. | |
| 2004/0167559 A1 * | 8/2004 | Taylor | A61B 17/3423 606/185 |
| 2004/0210304 A1 | 10/2004 | Seguin et al. | |
| 2005/0131349 A1 * | 6/2005 | Albrecht | A61B 17/34 604/167.06 |
| 2005/0137695 A1 | 6/2005 | Salahieh et al. | |
| 2005/0137697 A1 | 6/2005 | Salahieh et al. | |
| 2005/0165433 A1 | 7/2005 | Haberland et al. | |
| 2005/0216028 A1 * | 9/2005 | Hart | A61B 17/3498 606/108 |
| 2006/0074484 A1 | 4/2006 | Huber | |
| 2006/0106415 A1 | 5/2006 | Gabbay | |
| 2006/0142848 A1 | 6/2006 | Gabbay | |
| 2006/0167468 A1 | 7/2006 | Gabbay | |
| 2006/0259120 A1 | 11/2006 | Vongphakdy et al. | |
| 2007/0010876 A1 | 1/2007 | Salahieh et al. | |
| 2007/0027534 A1 | 2/2007 | Bergheim et al. | |
| 2007/0043435 A1 | 2/2007 | Seguin et al. | |
| 2007/0055358 A1 | 3/2007 | Krolik et al. | |
| 2007/0073391 A1 | 3/2007 | Bourang et al. | |
| 2007/0088431 A1 | 4/2007 | Bourang et al. | |
| 2007/0112422 A1 | 5/2007 | Dehdashtian | |
| 2007/0162100 A1 | 7/2007 | Gabbay | |
| 2007/0168013 A1 | 7/2007 | Douglas | |
| 2007/0203575 A1 | 8/2007 | Forster et al. | |
| 2007/0239271 A1 | 10/2007 | Nguyen | |
| 2007/0244552 A1 | 10/2007 | Salahieh et al. | |
| 2008/0071369 A1 | 3/2008 | Tuval et al. | |
| 2008/0086080 A1 * | 4/2008 | Mastri | A61B 17/3421 604/95.03 |
| 2008/0147182 A1 | 6/2008 | Righini et al. | |
| 2008/0306442 A1 | 12/2008 | Bardsley et al. | |
| 2009/0030375 A1 | 1/2009 | Franer et al. | |
| 2009/0054975 A1 | 2/2009 | del Nido et al. | |
| 2009/0248033 A1 * | 10/2009 | Forsell | A61B 17/12009 606/127 |
| 2009/0270813 A1 * | 10/2009 | Moreno, Jr. | A61B 17/3462 604/167.01 |
| 2009/0270817 A1 * | 10/2009 | Moreno | A61B 17/3462 604/264 |
| 2010/0004740 A1 | 1/2010 | Seguin et al. | |
| 2010/0286768 A1 | 11/2010 | Alkhatib | |
| 2010/0298931 A1 | 11/2010 | Quadri et al. | |
| 2011/0004046 A1 * | 1/2011 | Campbell | A61M 1/101 600/16 |
| 2011/0224678 A1 | 9/2011 | Gabbay | |
| 2014/0243794 A1 * | 8/2014 | Halskov | A61M 3/005 604/514 |
| 2015/0238718 A1 * | 8/2015 | Schnell | A61F 2/20 128/202.27 |

FOREIGN PATENT DOCUMENTS

| | | |
|---|---|---|
| EP | 1926455 A2 | 6/2008 |
| WO | 9732623 A1 | 9/1997 |
| WO | 07071436 A2 | 6/2007 |
| WO | 08070797 A2 | 6/2008 |
| WO | 10051025 A1 | 5/2010 |
| WO | 10087975 A1 | 8/2010 |

OTHER PUBLICATIONS

Ruiz, Carlos, Overview of PRE-CE Mark Transcatheter Aortic Valve Technologies, Euro PCR (2010).
Quaden, Rene et al., Percutaneous aortic valve replacement: resection before implantation, 836-840, Quaden, Rene et al., European J. of Cardio-thoracic Surgery, 27 (2005).

* cited by examiner

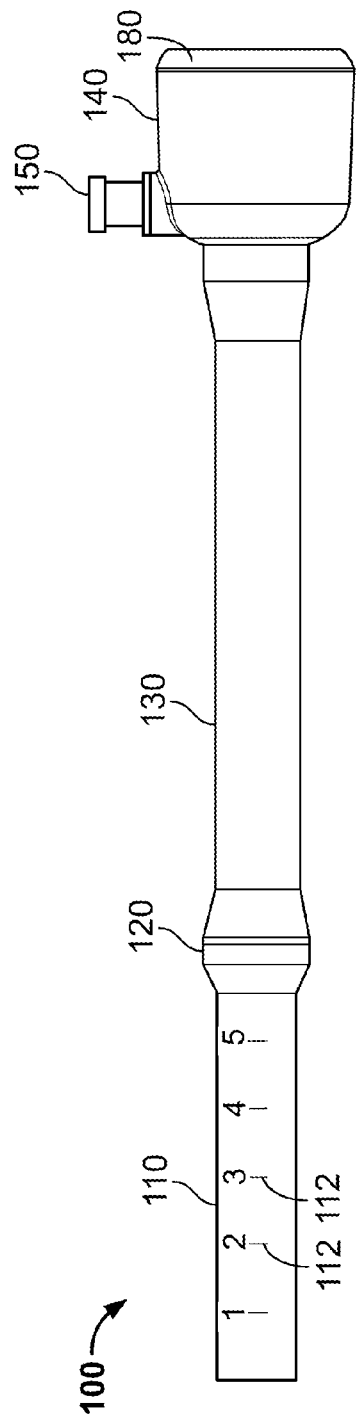
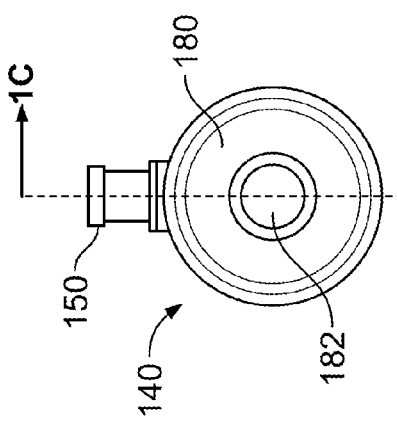
FIG. 1A
FIG. 1B

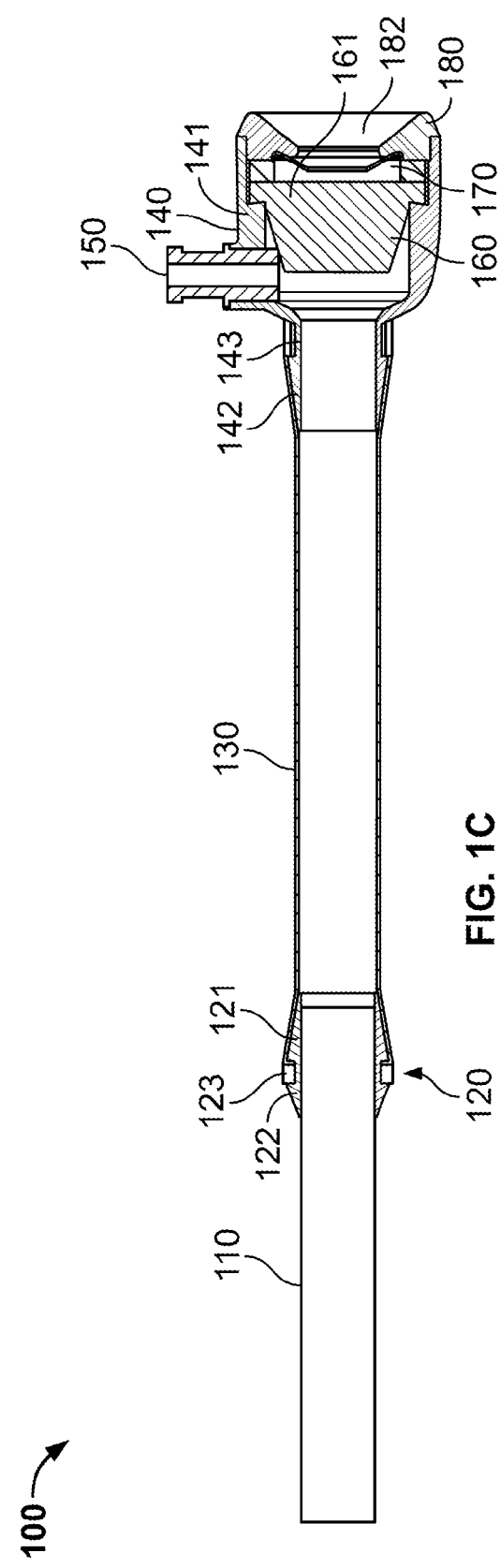

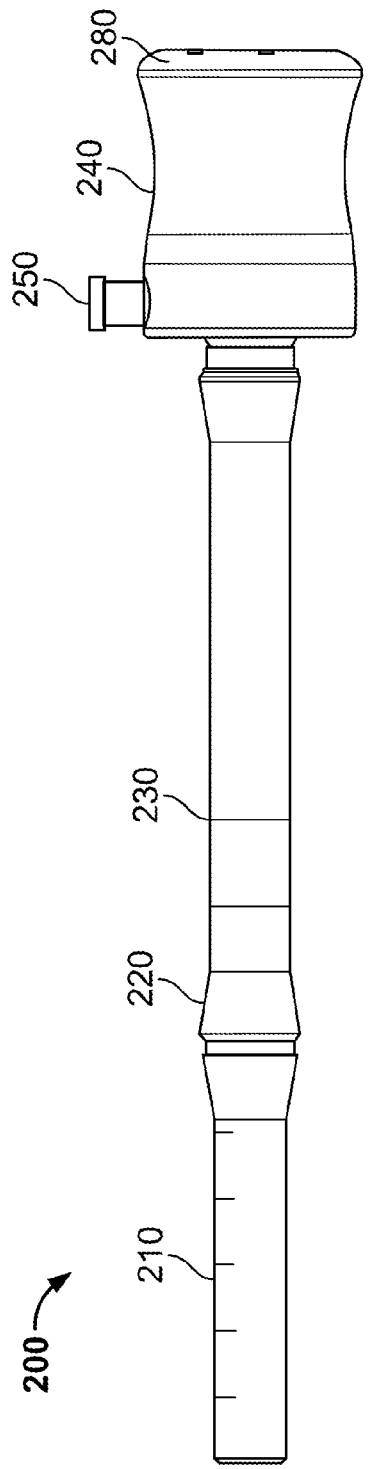
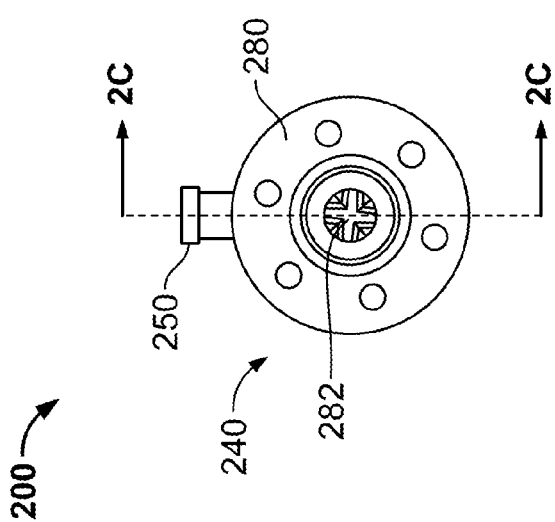
FIG. 2A
FIG. 2B

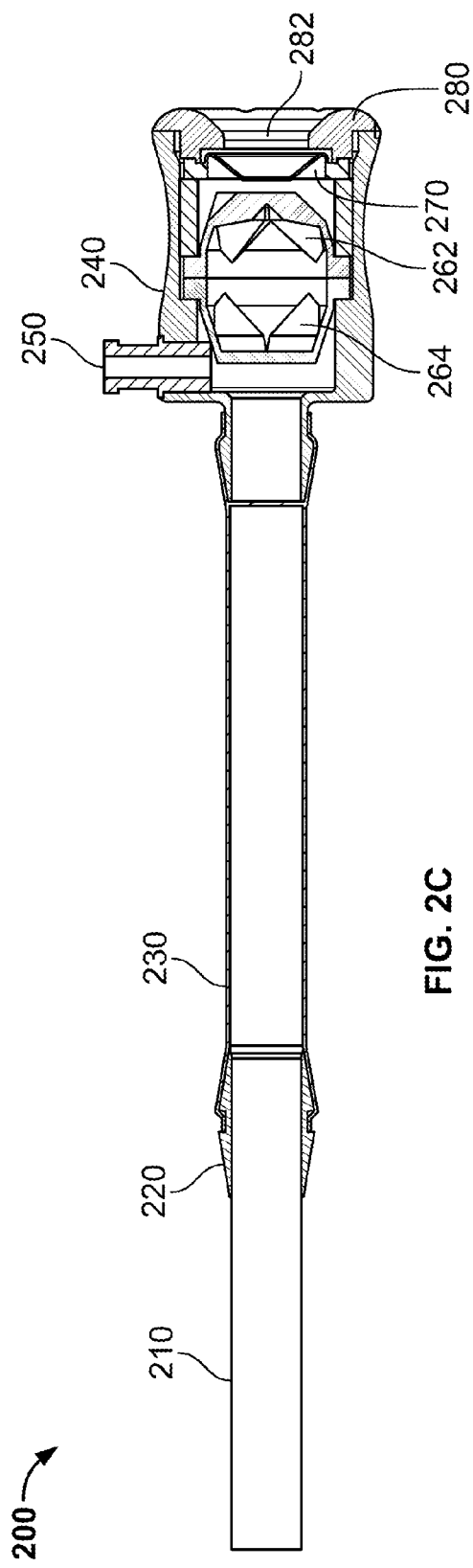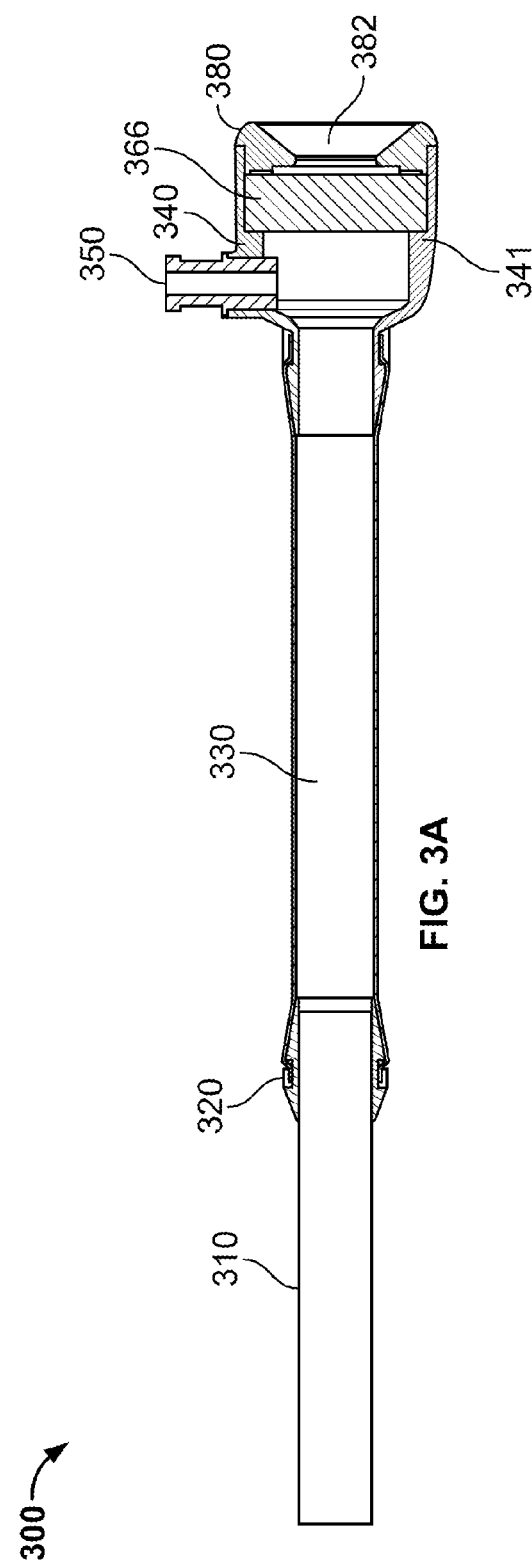

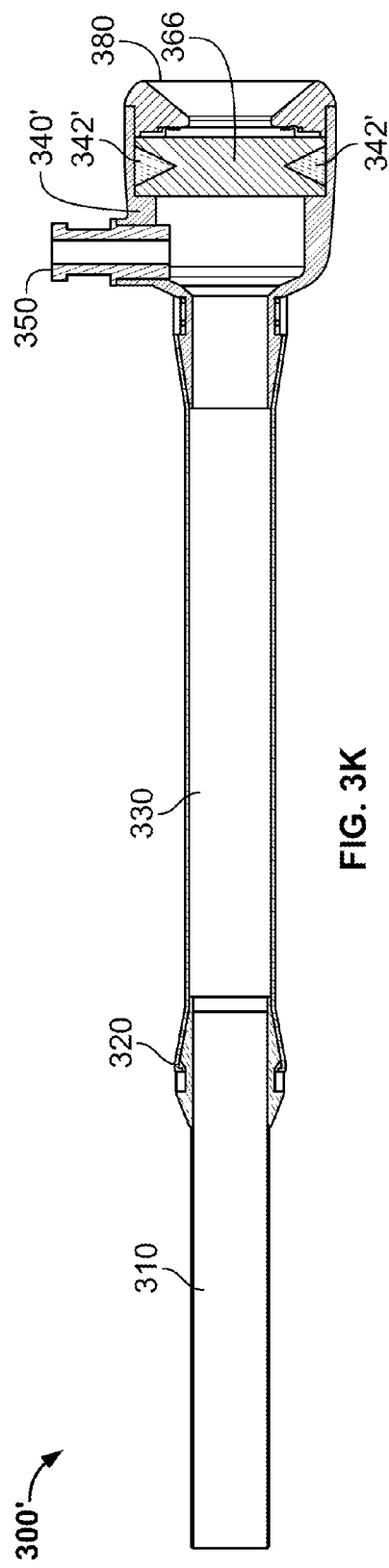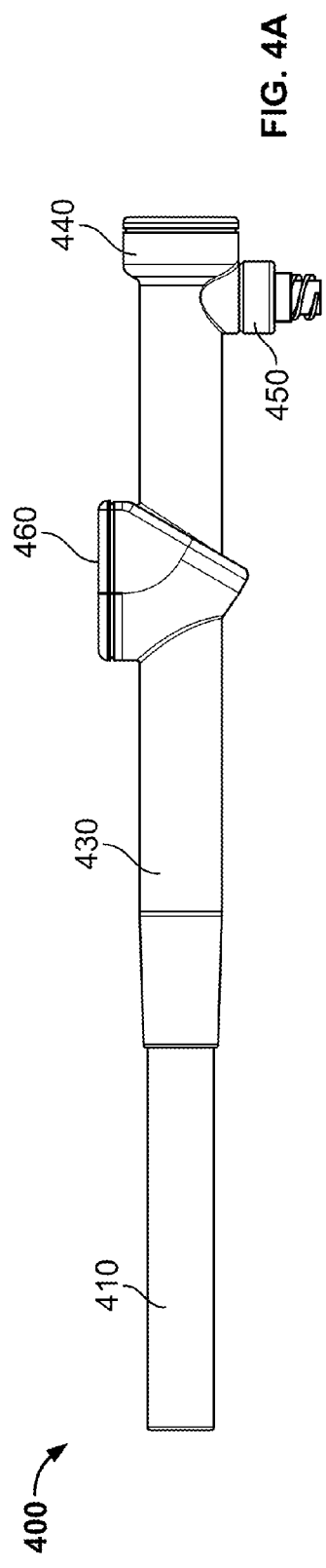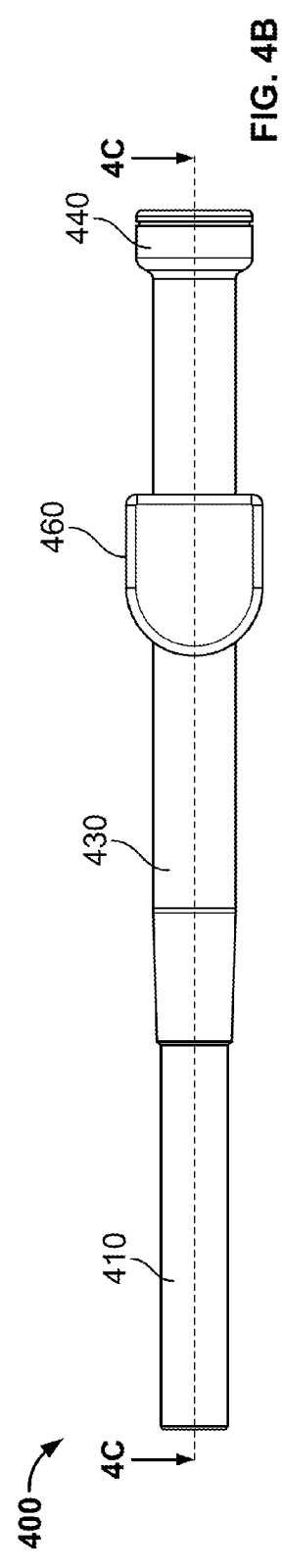

TRANSAPICAL INTRODUCER

CROSS-REFERENCE TO RELATED APPLICATIONS

The present application is a national phase entry under 35 U.S.C. § 371 of International Application No. PCT/US2014/042494, filed Jun 16, 2014, published in English, which claims priority from U.S. Provisional Application No. 61/836,440, filed Jun 18, 2013, all of which are hereby incorporated herein by reference.

BACKGROUND

During a cardiac valve repair or replacement procedure, access to the interior of the heart may be necessary. To access the interior of the heart, physicians often conduct a median sternotomy. In a median sternotomy, the physician makes an incision along the center of the chest to divide the patient's sternum, thereby creating an access to the heart. Sternotomies may result in long recovery times and involve a high risk of complications (e.g., infections) due to the lengthy surgery required for these unstable patients.

Rather than performing the more invasive median sternotomy, a less invasive thoracotomy introducer device may be used to access the interior of the heart and to provide a conduit through which other devices may be passed during the procedure. Such miniaturized introducers aid the physician in inserting the necessary repair or replacement materials into the heart while also limiting the level of physical invasiveness and the amount of blood loss.

BRIEF SUMMARY

In one embodiment, an introducer includes a housing near a proximal end of the introducer, a first valve in the housing, a flexible proximal tube coupled to the housing, and a rigid distal tube coupled to a distal end of the proximal tube. The proximal tube may be more flexible than the distal tube and may be capable of being clamped to prevent fluid flow therethrough.

In another embodiment, an introducer includes a housing near a proximal end of the introducer, a foam seal located in the housing, a flexible proximal tube coupled to the housing, and a rigid distal tube coupled to a distal end of the proximal tube. The proximal tube may be more flexible than the distal tube and may be capable of being clamped to prevent fluid flow therethrough.

In a further embodiment, an introducer includes an introducer housing near a proximal end of the introducer, a first tube coupled to the introducer housing, a valve housing on the first tube, and a flap hingedly connected to the valve housing. The flap may have a first closed position and a second open position. When in the first closed position, a proximal end of the first tube may be fluidly sealed from a distal end of the first tube and, when in the second open position, the proximal end of the first tube may be in fluid communication with the distal end of the first tube.

BRIEF DESCRIPTION OF THE DRAWINGS

FIG. 1A is a side plan view of one embodiment of a transapical introducer.

FIG. 1B is a front plan view of the transapical introducer of FIG. 1A.

FIG. 1C is a cross sectional view of the transapical introducer of FIG. 1B taken along line 1C-1C.

FIG. 2A is a side plan view of another embodiment of a transapical introducer.

FIG. 2B is a front plan view of the transapical introducer of FIG. 2A.

FIG. 2C is a cross sectional view of the transapical introducer of FIG. 2B taken along line 2C-2C.

FIG. 3A is a cross sectional view of a further embodiment of a transapical introducer.

FIG. 3K is a cross sectional view of an alternate embodiment of a transapical introducer with a foam seal.

FIG. 4A is a side plan view of a transapical introducer according to a further embodiment.

FIG. 4B is a top plan view of the transapical introducer of FIG. 4A.

DETAILED DESCRIPTION

Figure 1D:
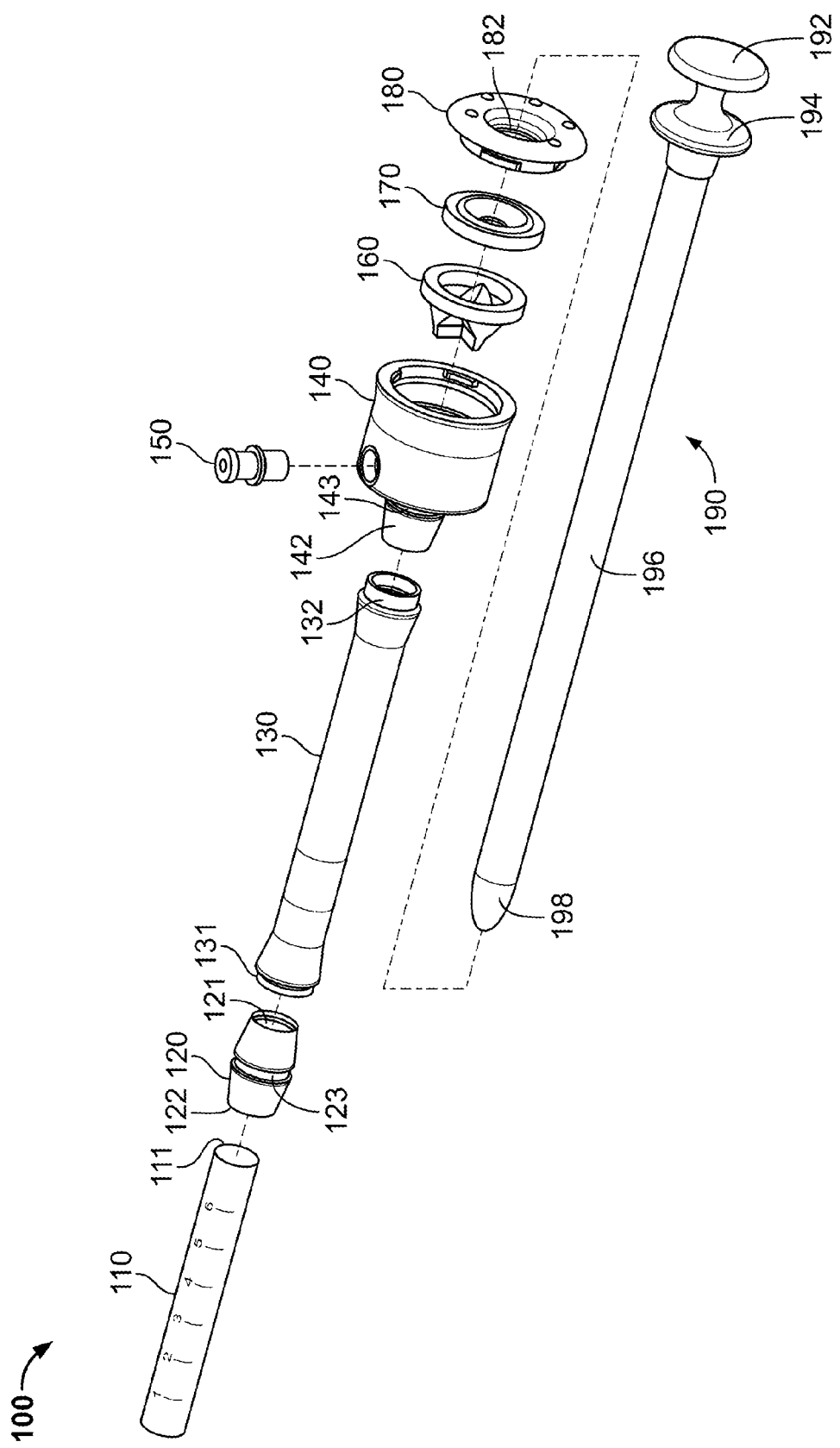
FIG. 1D is an exploded view of the transapical introducer of FIG. 1A with an obturator.

As used herein, the term "proximal," when used in connection with an introducer device, refers to an end of the device closer to the user of the device. On the other hand, the term "distal," when used in connection with an introducer device, refers to an end of the device farther away from the user. In the figures, like numbers refer to like or identical parts.

The present disclosure generally relates to transapical introducers for use in procedures repairing or replacing heart valve (e.g. mitral or aortic valves, such as percutaneous mitral valve repair ("PMVR")). However, the transapical introducers disclosed herein may be used with other transapical devices and procedures.

Generally, during a transapical procedure, a surgeon gains access to the heart by sewing a purse string suture at the apex of the heart and creating an access opening, as is known in the art. An introducer is inserted into the heart and the purse string suture is cinched, or drawn, about the introducer. The particular treatment procedure, such as PMVR, is performed, inserting devices as necessary through the introducer and into the heart. Once the particular treatment procedure is concluded, any remaining devices are removed through the introducer, and the introducer itself is removed. The incision in the heart is closed, completing the treatment procedure.

Some less invasive introducers have been developed over the years. Improvements to these introducers are nonetheless still possible and desirable. Such improvements may be directed at, for example, reducing the likelihood of forming air bubbles within the introducer that could potentially, and dangerously, enter the heart, or providing a user with more intuitive control of the introducer. For example, providing a clear introducer may help a user visualize air bubbles trapped inside the introducer. Further, introducers that include flexible portions may be clamped shut to fluidly seal an introducer after a device has been removed from the introducer. This may help ensure that no air enters the introducer between the time after a user removes a first device from the introducer seal and before the user inserts a second device into the introducer. Still further, providing a biased valve that opens only when a device is inserted through the introducer and closes after the device is removed from the introducer may help reduce the likelihood of air bubbles becoming trapped in the introducer.

Now referring to FIGS. 1A-D, various views of one embodiment of a transapical introducer 100 are illustrated. The introducer 100 generally includes a hollow distal tube 110 connected to a hollow proximal tube 130 by a connector 120. The connector 120 may, for example, be generally tubular with a through-hole extending from a proximal connector end 121 to a distal connector end 122. The proximal and distal connector ends 121, 122 may each be frustoconical and may be separated by a groove 132. A distal end 131 of the hollow proximal tube 130 may be configured to stretch over the proximal connector end 121 and to snap or otherwise mate with the groove 132 in the connector 120. A proximal end 111 of the hollow distal tube 110 may be inserted into the through-hole of the connector 120 via the distal connector end 122. Connected to the proximal tube 130 is a housing 140. The housing 140 may include a number of additional components, including, for example, a flush port 150, a duckbill valve 160, a wiper seal 170, and a housing cap 180 (see FIGS. 1C and 1D). An obturator 190 or similar device may be used with the introducer 100.

The distal tube 110 may be formed of a rigid material to provide radial strength during apex introduction and also during insertion of devices through the distal tube. The distal tube 110 may include one or more depth markers 112 to indicate the distance from the distal end of the distal tube 110. A distal end 131 of the proximal tube 130 is attached to the proximal end 111 of the distal tube 110. The proximal tube 130 may be flexible to allow the proximal tube to be clamped, for example with a hemostatic clamp, to seal fluid from flowing through the introducer 100. An exemplary hemostatic clamp is described more fully below with reference to FIG. 1I. One or both of the distal tube 110 and proximal tube 130 may be formed from a translucent, transparent, or otherwise clear material. As used herein, the terms "translucent," "transparent," and "clear" refer generally to the ability of light to pass through a first object such that a second object may be seen through the first object. The terms are intended to be interchangeable as used in this disclosure. By forming the proximal tube 130 from a translucent material, a user will be able to see, for example, air bubbles in the proximal tube, as well as devices inserted through the proximal tube, such as the obturator 190 or other devices.

Illustrative materials that may be used for the distal tube 110 include, for example, biocompatible materials such as stainless steel, carbon reinforced nylon, or composite wound tubing. The material used for the distal tube 110 may be chosen based, in part, on the stiffness of the material. For example, materials with a modulus of elasticity of greater than about 190 GPa, including steel, may be suitable. Further, materials with a modulus of elasticity of greater than about 100 GPa, such as titanium alloys, may be suitable for the distal tube 110. Still further, materials with a modulus of elasticity of greater than about 40 GPa, such as magnesium alloys, may be suitable for the distal tube 110. In one embodiment, the distal tube 110 is formed of a material with a modulus of elasticity greater than about 10 GPa.

Illustrative materials that may be used for the proximal tube 130 include, for example, biocompatible materials such as polytetrafluoroethylene ("PTFE"), polyfluoroethylene ("PFE"), polyurethane ("PU"), or polyethylene ("PE"). The material used for the proximal tube 130 may be chosen based, in part, on the stiffness of the material. For example, materials with a modulus of elasticity of between about 0.35 GPa and about 1.75 GPa may be suitable for the proximal tube 130. In another example, materials with a modulus of elasticity of between about 0.5 and about 1 GPa may be suitable for the proximal tube 130. Other materials may be suitable for the proximal tube 130, particularly materials that are pliable enough to allow the proximal tube 130 to close on itself under clamping force and recover to its original shape without cracking, splitting, or otherwise breaking.

The housing 140 may take the form of a general hollow tube with an extension 142 extending from a distal end of the housing 140. The extension 142 may be generally frustoconical with a circular groove 143 at a proximal end of the extension 142. The distal end of the housing 140 may be attached to a proximal end 132 of the hollow proximal tube 130. For example, the proximal end 132 of the hollow proximal tube 130 may be stretched over the extension 142 of the housing 140 and snap or otherwise mate with the groove 143 to secure the proximal tube 130 to the housing 140. The housing 140 may include a flush port 150 proximal to the extension 142. The housing 140 may include a duckbill valve 160 proximal to the flush port 150, a wiper seal 170 proximal to the duckbill valve 160, and a housing cap 180 proximal to the wiper seal 170. An interior of the housing 140 may take forms other than a tube or cylinder. For example, the housing 140 may include a shoulder 141 in the form of an annulus to help keep components of the housing 140 in place. For example, the duckbill valve 160 may include an annular flange 161 that abuts the shoulder 141 of the housing 140 to help the duckbill valve 160 from shifting positions.

Figure 1F:
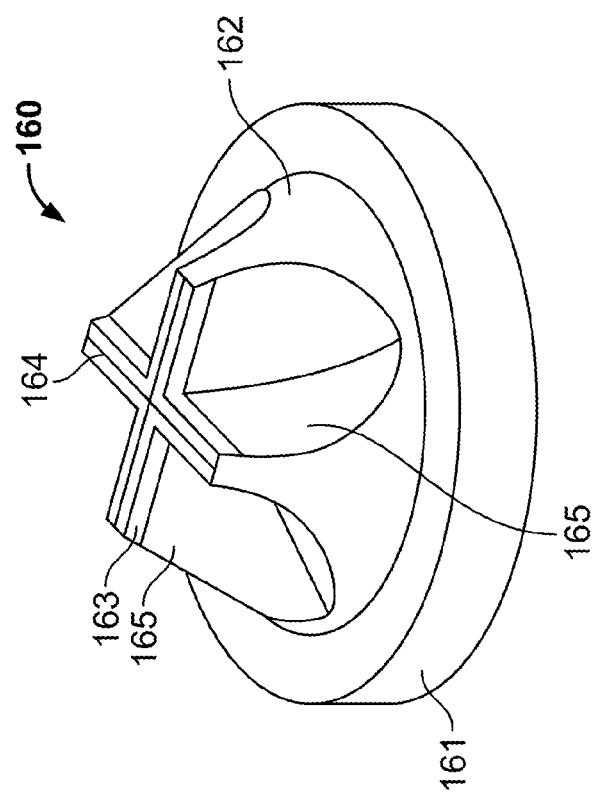
FIG. 1F is a perspective view of another embodiment of a duckbill valve according to an aspect of the disclosure.
Figure 1E:
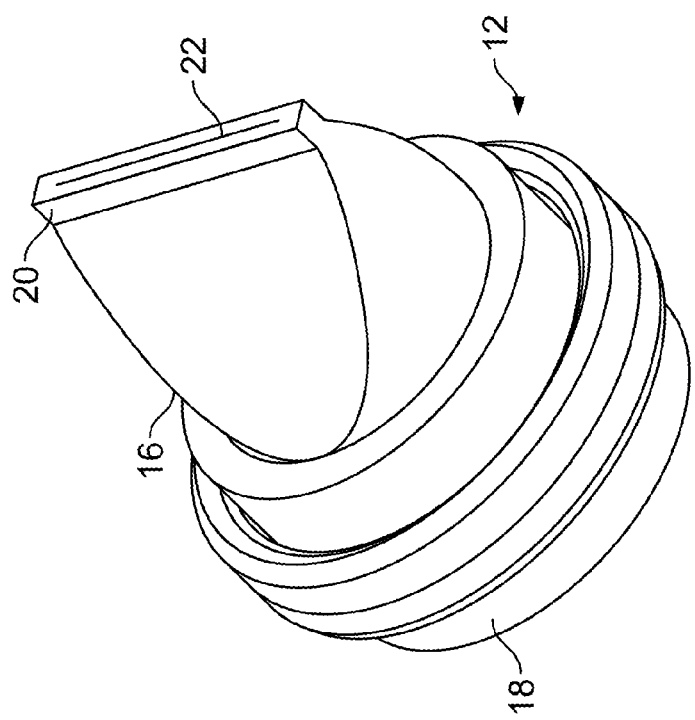
FIG. 1E is a perspective view of a duckbill valve according to the prior art.

In the embodiment illustrated in FIGS. 1A-D, a first seal takes the form of duckbill valve 160. More specifically, the duckbill valve takes the form of the quad-slit duckbill valve 160. Duckbill valves are known in the art. A traditional duckbill valve 12, as illustrated in FIG. 1E, generally is made of pliable material, shaped like the beak of a duck, and is configured with a duckbill portion 16 and a base portion 18. The duckbill portion 16 is configured with a flattened end 20 having a slit 22 to flex open so as to allow and provide fluid to pass through, and to close to prevent the backflow of the fluid. For example, in operation when a fluid is pumped through the duckbill portion 16, the flattened end 20 opens to permit the pressurized fluid to pass; and when internal pressure is removed, the duckbill end 20 returns to its flattened shape, closing the slit 22, thus preventing backflow. The operation of the duckbill valve 12 is similar to a mitral valve. Further, the base portion 18 may be configured with an external circumferential protruding portion, such as a sealing ring or bead, for coupling the duckbill valve 12 to another device, such as a supply line or pump (not shown) that provides fluid.

The quad-slit duckbill valve 160 is similar to the duckbill valve 12, but has four flaps instead of two, the four flaps coapting together to close the valve. The duckbill valve 160 may be configured with a duckbill portion 162 and a base portion or flange 161. The duckbill portion 162 includes four leaflets or flaps 165, and is configured with a flattened end 163 having a slit 164 to flex open so as to allow and provide fluid to pass through, and to close to prevent the backflow of the fluid. The duckbill valve 160 operates in essentially the same manner as duckbill valve 12, with the flattened end 163 opening to permit pressurized fluid to pass; and when internal pressure is removed, the duckbill end 163 returns to its flattened shape, closing the slit 164, thus preventing backflow. The flange 161 may, for example, be used in combination with the shoulder 141 of the housing 140 to help keep the duckbill valve 160 in place.

For a given diameter, the traditional duckbill valve 12 may require a certain length of each flap in order to effectively function as a one-way valve. For that same diameter, the duckbill valve 160 may require a shorter length for each flap 165 to effectively function as a one-way valve. The use of the duckbill valve 160 provides for less dead-space within the housing 140, and generally allows for the housing to be a shorter overall length. Although illustrated as a quad-slit duckbill valve 160, other valves, including traditional duckbill valves 12 or three-sided duckbill valves may be used with the introducer 100.

Figure 1H:
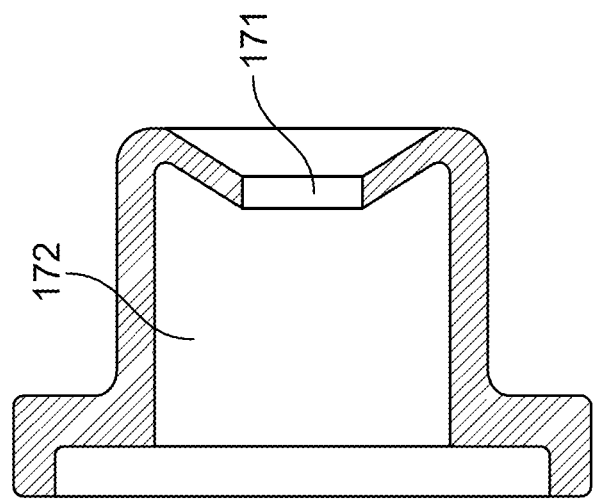
FIG. 1H is a cross sectional view of the wiper seal of FIG. 1G taken along the line 1H-1H.
Figure 1G:
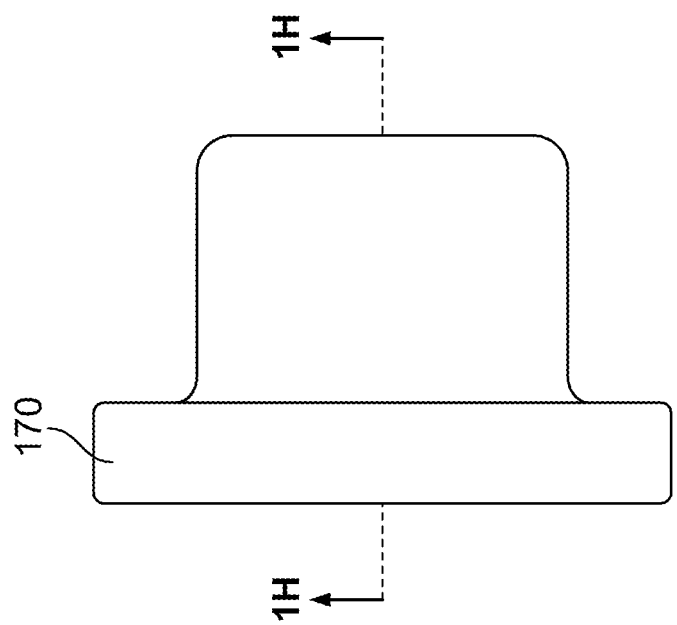
FIG. 1G is a side plan view of a wiper seal according to the prior art.

Proximal to the duckbill valve 160 is a second seal, which takes the form of a wiper seal 170. Wiper seals are known in the art. For example, FIGS. 1G and 1H illustrate a wiper seal 70 according to the prior art. The prior art wiper seal 70 includes a partial sealing and cleaning mechanism 71 located at the center of a lumen 72 which allows a device to pass with little drag or frictional force on the device. The sealing and cleaning mechanism 71 can be pre-treated with a sterilizing agent or an anti-coagulant, e.g., heparin. As a device, such as the obturator 190, is passed through the wiper seal 70, the sealing and cleaning mechanism 71 remains closed around the device and may simultaneously "wipe" or scrape the device to prevent air from seeping into the introducer 100, while further preventing dirt or other contaminants on the device from entering the introducer 100. Although one particular embodiment of a prior art wiper seal 70 is illustrated in FIGS. 1G and 1H, the wiper seal 170 of the introducer 100 may take other configurations.

The housing 140 may also include a flush port 150 distal of the duckbill valve 160. Flush ports are known in the art. The flush port 150 brings the distal tube 110 and proximal tube 130 in fluid communication with the outside of the housing 140 distally of the duckbill valve 160. The flush port 150 allows a user to introduce a fluid, such as saline, into the proximal tube 130 and distal tube 110 after a device, such as the obturator 190, has been inserted through the proximal and distal tubes. This may be done, for example, to remove air trapped within the introducer. Similarly, the flush port 150 may be used to withdraw fluid, such as saline, blood, and/or air.

The proximal end of the housing 140 includes a housing cap 180. The housing cap 180 closes off the proximal end of the housing 140, with the exception of a central opening 182 that allows for devices, such as the obturator 190, to be inserted into the introducer 100. The housing cap 180 may have a chamfered surface that may direct devices, such as the obturator 190, to the central opening 182.

In practice, the obturator 190 is advanced through the central opening 182 in the housing cap 180 prior to inserting the introducer 100 into the heart. This may be accomplished, for example, by grasping a handle 192 of the obturator 190 and manually pushing the obturator through the introducer until a lip 194 of the obturator makes contact with the housing cap 180, limiting further distal movement of the obturator. The shaft 196 of the obturator may be sized to substantially match an inner diameter of the distal tube 110 and/or proximal tube 130. This sizing allows the obturator 190 to limit the ability of fluid, such as blood, to flow out of the heart and through the introducer 100 after the introducer has been inserted into the heart. However, it should be understood that the obturator 190, as well as other devices, may not fit perfectly within the introducer 100. Even when the obturator 190 or other device is inserted fully within the introducer 100, gaps may remain along at least some of the length of the introducer 100 between the outside of the obturator 190 (or other device) and the inside of the distal tube 110 and/or proximal tube 130 of the introducer 100. Fluids, such as air, may reside in these gaps if not purged from the introducer 100. The tip 198 of the obturator 190 may be tapered. The tapered shape of the tip 198 may aid the user in guiding the obturator 190 through the housing 140 and components therein.

With the obturator 190 inside the introducer 100, the user may flush the introducer to remove air trapped in the housing 140, the proximal tube 130, or the distal tube 110. In one example, the user may attach a 40 cc syringe to the flush port 150 and flush the introducer 100 with sterile saline. Flushing may be continued until a saline stream comes out of the distal end of the distal tube 110 of the introducer 100. This first flush is performed prior to inserting the introducer 100 into the heart.

After flushing, the introducer 100 is inserted into the heart far enough that a portion of the distal tube 110 crosses the heart tissue, with the entire proximal tube 130 and the housing 140 remaining outside of the heart. The introducer 100 may be inserted into the heart at an angle, such that the proximal end of the introducer 100 is higher than the distal end of the introducer. In this position, air bubbles trapped in the introducer tend to move away from the heart.

Once the introducer 100 is at the desired position in the heart, the obturator 190 is slowly withdrawn from the introducer. Because the obturator 190 is sized to fill much of the space within the distal tube 110 and proximal tube 130, withdrawal of the obturator may create negative pressure causing blood to flow from the heart into the introducer 100. The proximal tube 130 may include one or more indicia to provide a user with, for example, a visual marking corresponding to a desired distance to withdraw the obturator 190. If a marking is provided on the proximal tube 130, the user may remove the obturator 190 until the distal end of the tip 198 of the obturator aligns with the marking. As described above, the proximal tube 130 may be translucent to facilitate the ability of the user to determine the position of the obturator 190 in the proximal tube 130.

When the obturator 190 has been withdrawn to the desired position within the introducer 100, the user may clamp the proximal tube 130, for example with a hemostatic clamp. This clamping is made possible, at least in part, due to the proximal tube 130 being flexible, as described above. Further, because the proximal tube 130 is translucent, the user may accurately determine a desired location for clamping. This location may be based, in part, on the location of the obturator 190 in the proximal tube 130. Even further, any air bubbles created during clamping may be able to be visually identified and dealt with, for example, by clamping in a different location or taking other appropriate actions. After clamping, a user may also flush the introducer 100, using the flush port 150 as described above to minimize the likelihood of any air bubbles being trapped within the introducer 100. If the user is satisfied with the clamping of the proximal tube 130, he may fully remove the obturator 190 from the introducer 100 and begin the treatment procedure.

Figure 1I:
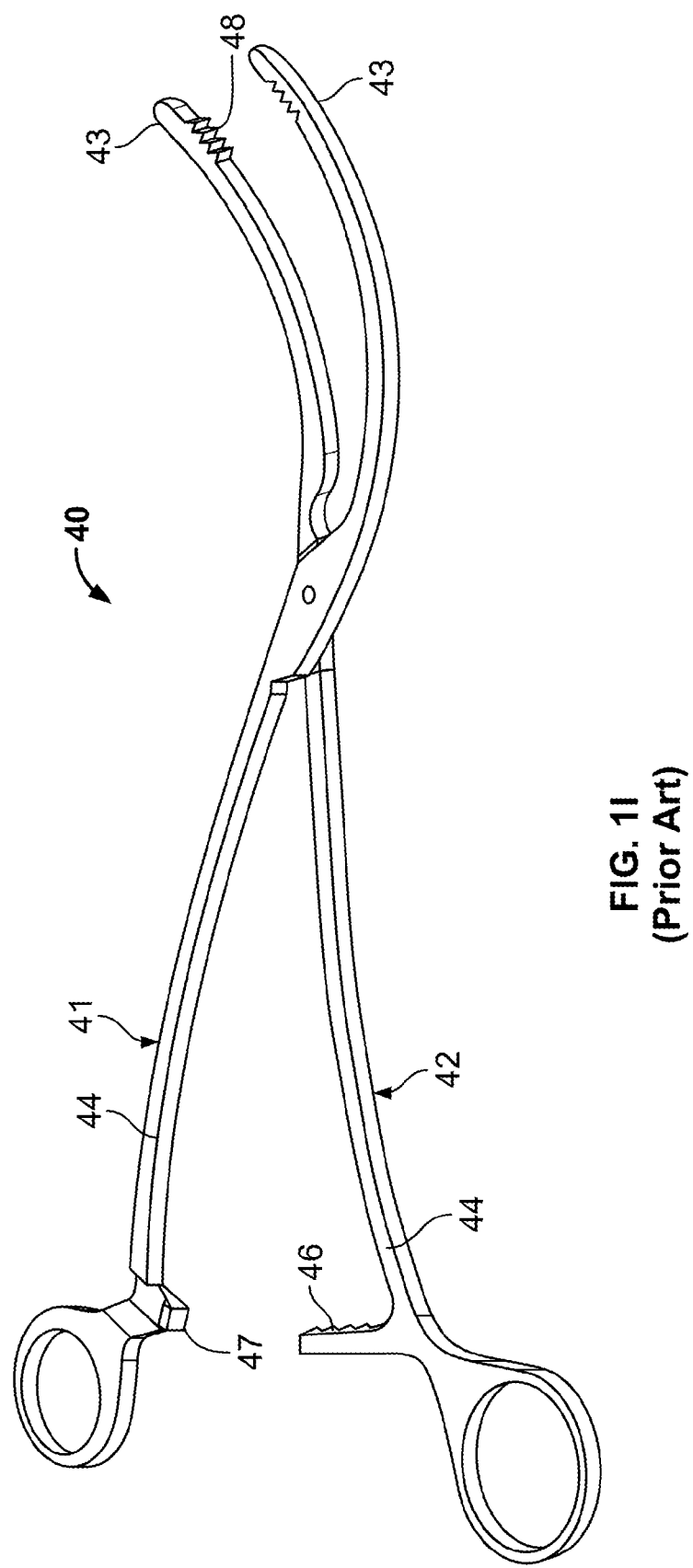
FIG. 1I is a perspective view of a hemostatic clamp according to the prior art.

Referring to FIG. 1I, a hemostatic clamp 40 according to the prior art is illustrated. The hemostatic clamp 40 may be made of, for example, titanium alloy. The hemostatic clamp 40 may include a left clamp body 41 and a right clamp body 42 which are joined by a hinge and may be divided into jaws 43 and handles 44 by the hinge. The jaws 43 of the left and right clamp bodies 41, 42 may have a curved configuration with ends extending upwardly. A serrated portion 48 with serrations projecting from an engaging surface are respectively formed on both ends of the jaw 43 of the left clamp body 41 and the jaw 43 of the right clamp body 42. The handles 44 of the left and right clamp bodies 41, 42 respectively may have a clamping force adjustment mechanism acting in cooperation with each other. The adjustment mechanism may include a ratchet means 46 formed on one of the left clamp body 41 and the right clamp body 42 and a pawl 47 formed on the other of the left clamp body 41 and the right clamp body 42. Other hemostatic clamps, such as those with different shapes, different force adjustment mechanisms, and with or without serrations may alternately be used in conjunction with the introducer 100.

Treatment procedures that may be performed using the introducer 100 include PMVR or transcatheter aortic valve repair ("TAVR"). It should be noted, however, that the introducer 100 may be used with a number of other procedures, including other minimally invasive heart procedures.

Figure 1J:
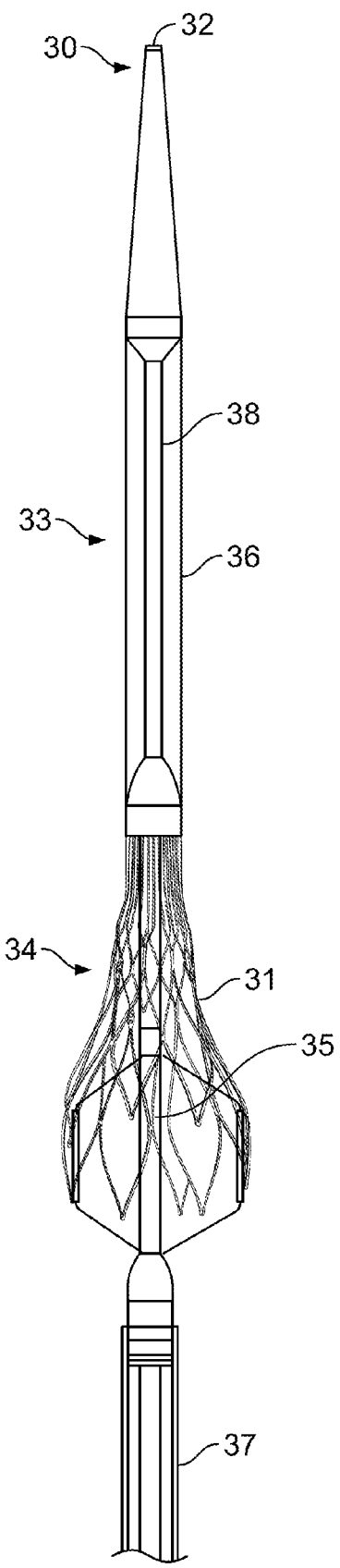
FIG. 1J is a side plan view of a transapical delivery device according to the prior art.

One exemplary delivery device that could be used with the introducer 100 is a transapical heart valve delivery device 30, illustrated in FIG. 1J. The transapical delivery device 30 for a collapsible prosthetic heart valve 31 extends from an atraumatic tip 32 at the distal end of the device to a proximal end (not shown), and includes a catheter assembly 33 for delivering the heart valve to, and deploying the heart valve at, a target location. The catheter assembly 33 is adapted to receive the collapsible prosthetic heart valve 31 in an assembled condition in a compartment 34 defined around a support shaft 35. A distal sheath 36 is operable for sliding movement between a closed position covering the prosthetic heart valve 31 and maintaining it in a collapsed condition, and an open position for deployment of the valve.

The delivery device further includes an outer shaft 37, the distal end of which is connected to a valve retainer, and the proximal end of which can optionally be connected to a hub (not shown) that can be held by a user when sliding the distal sheath 36 relative to the support shaft 35. An inner shaft 38 extends from the proximal end of the delivery device through the outer shaft 37 and the support shaft 35 for connection to the atraumatic tip 32.

The distal sheath 36 surrounds the support shaft 35 when the distal sheath is in the closed position, and is slidable relative to the support shaft such that it can selectively cover or uncover the compartment 34. The distal sheath 36 is connected at its distal end to the atraumatic tip 34, such that sliding movement of the inner shaft 38 controls the movement of the distal sheath both proximally and distally, which in turn controls the expansion of the heart valve 31.

If performing a transapical TAVR procedure, the transapical delivery device 30 is inserted through the central opening 182 in the housing 180, through the wiper seal 170, and through the duckbill valve 160. The tip of the transapical delivery device 30 is advanced until it is near the clamped area of the proximal tube 130. The proximal tube 130 and housing 140 may be flushed with, for example, saline using a 40 cc syringe coupled to the flush port 150. The saline fills the introducer 100 proximal to the clamped area of the proximal tube 130, forcing air out of the introducer. Depending on the particular device being used, the flushing step may also flush the delivery device itself. For example, delivery devices often contain lumens that should be purged of air with a flushing step prior to the delivery device being inserted into a patient. These delivery devices may include their own features for flushing, such as additional flush ports and/or purge holes, which may be used in conjunction with or separate to the flushing of the introducer 100 as appropriate. For example, if the delivery system includes purge holes on its shaft, the flush port 150 may be used to remove any air from the proximal tube 130 and delivery device, with flushing continued until saline runs out the purge holes on the delivery system shaft that are positioned proximal to the wiper seal 170.

After purging, the user may visually confirm that there are no identifiable air bubbles remaining in the proximal tube 130. Once confirmed, the hemostatic clamp 40 is removed from the proximal tube 130, and the delivery device may be advanced into the heart. If the delivery device contains purge holes, the purge holes are advanced past the wiper seal 170 during advancement of the delivery device such that air cannot enter the heart through the purge holes. The particular treatment procedure, such as TAVR, is performed as is known in the art. During the treatment procedure, the delivery device may need to be removed and replaced, either with the same or another device. If this replacement is required, the user may repeat the flushing and clamping steps described above to minimize the likelihood of introduction of air bubbles into the heart. Once the treatment procedure is complete, the user may remove any devices in the introducer 100, and remove the introducer itself from the heart while using the purse string sutures to close the incision.

Now referring to FIGS. 2A-C, various views of another embodiment of a transapical introducer 200 are illustrated. The introducer 200 generally includes a hollow distal tube 210 connected to a hollow proximal tube 230 by a connector 220. These elements are substantially similar to the distal tube 110, the proximal tube 130, and connector 120 described in relation to the introducer 100 above. For example, the distal tube 210 may be formed of a rigid material. Similarly, the proximal tube 230 may be flexible to allow the proximal tube to be clamped, without cracking, splitting, or otherwise breaking, in order to seal fluid from flowing through the introducer 200. One or both of the distal tube 210 and proximal tube 230 may be formed from a translucent, transparent, or otherwise clear material. Connected to the proximal tube 230 is a housing 240. The housing 240 is similar to the housing 140 described in relation to the introducer 100, although the housing 240 may be differently shaped to appropriately house components contained therein. The components in the housing 240, as illustrated in FIG. 2C, may include, for example, a flush port 250, first and second duckbill valves 262, 264 proximal to the first duckbill valve, a wiper seal 270 proximal to the first and second duckbill valves, and a housing cap 280 proximal to the wiper seal. Similar to the housing cap 180, the housing cap 280 may be chamfered toward a central opening 282 in the housing cap to allow devices to enter the introducer 200. The wiper seal 270 may be similar or identical to the wiper seal 170 described above in relation to FIGS. 1A-D and 1G-H.

In the embodiment illustrated in FIGS. 2A-C, first and second seals take the form of duckbill valves. Although the duckbill valves may take different forms, such as the two-sided, three-sided or four-sided described above in relation to FIGS. 1A-F, the duckbill valves illustrated in FIGS. 2A-C take the form of the first quad-slit duckbill valve 262 and the second quad-slit duckbill valve 264. The structure of each quad-slit duckbill valve 262 and 264 is substantially similar to that described in relation to the quad-slit duckbill valve 160 of the introducer 100. For example, similar to the duckbill valve 160 illustrated in FIG. 1F according to an embodiment of the disclosure, the duckbill valves 262, 264 may each have a duckbill portion and a base/flange portion. The duckbill portion may include four leaflets or flaps and be configured with a flattened end having a slit to flex open so as to allow and provide fluid to pass through, and to close to prevent the backflow of the fluid. In the current embodiment, the first duckbill valve 262 is positioned in a similar manner as the position of the duckbill valve 160 of the introducer 100, with the first duckbill valve 262 being distal of both the housing cap 280 and the wiper seal 270. Stated another way, the first duckbill valve 262 may be positioned with a base or flange portion closer to the housing cap 280 and the flaps farther away from the housing cap. In this position, the first duckbill valve 262 allows fluid to pass from the proximal end of the introducer 200 toward the distal end, but not from the distal end to the proximal end. The second duckbill valve 264 is positioned distal to the first duckbill valve 262, as well as being distal to the housing cap 280 and the wiper seal 270, and faces the opposite direction of the first duckbill valve 262. In other words, the flaps of the first duckbill valve 262 face the flaps of the second duckbill valve 264. More specifically, the flaps of the second duckbill valve 264 are closer to the housing cap 280 than the base of the second duckbill valve.

The duckbill valve 262 functions substantially similar to the duckbill valve 160 described in relation to the introducer 100. The second duckbill valve 264 provides an additional level of sealing in the proximal direction. More specifically, the second duckbill valve 264 allows fluid to pass from the distal end of the introducer 200 toward the proximal end of the introducer, but not from the proximal end toward the distal end. This may be useful, for example, to help prevent air from being unintentionally forced into the introducer 200 if negative pressure is created in the proximal tube 230. Such negative pressure could be created, for example, by changes in flow or pressure in the heart when the distal tube 210 of the introducer 200 is in a ventricle of the heart. For example, when expelling blood, the left ventricle builds pressure prior to the aortic valve opening. Once the aortic valve opens, the high pressure in the ventricle causes the blood to pass from the left ventricle through the aorta. When the ventricle fills with blood, the filling is caused by low/negative pressure in the left ventricle, which causes blood to be drawn from the left atrium. When the ventricle is undergoing this cycle of pressure changes while the distal tube 210 of the introducer 200 is in the ventricle, the portion of the introducer in fluid communication with the ventricle may be affected by these pressure cycles. One specific concern is that, when the ventricle is at low or negative pressure, air may tend to be "sucked" into introducer 200 from the environment outside the introducer. The addition of the second duckbill valve 264 may alleviate or eliminate the tendency of air being sucked into the introducer 200 in such circumstances.

Other than the inclusion of the second duckbill valve 264, the remaining components of the introducer 200 may be similar or identical to the corresponding components describe in relation to the introducer 100. For example, the distal tube 210, the connector 220, the proximal tube 230, the flush port 250, the first duckbill valve 262, the wiper seal 270 and the housing cap 280 may all be similar or identical to the corresponding parts in the introducer 100. The housing 240, however, may be longer to accommodate the two duckbill valves 262, 264, whereas the housing 140 may only need to accommodate a single duckbill valve 160. Further, these components, other than the additional/second duckbill valve 264, function in the same or a similar fashion as described in relation to the first embodiment of the introducer 100.

Figure 3C:
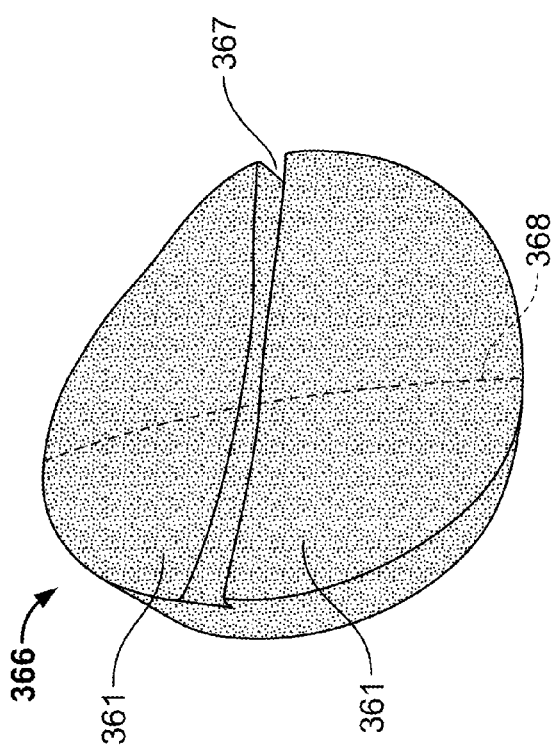
FIGS. 3C-E show multiple views of a foam seal of the transapical introducer of FIG. 3A.
Figure 3D:
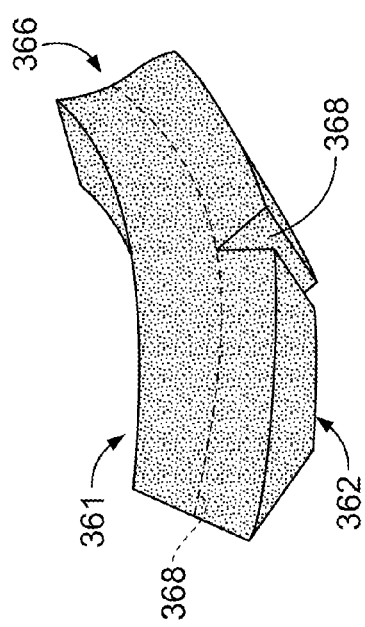
Figure 3B:
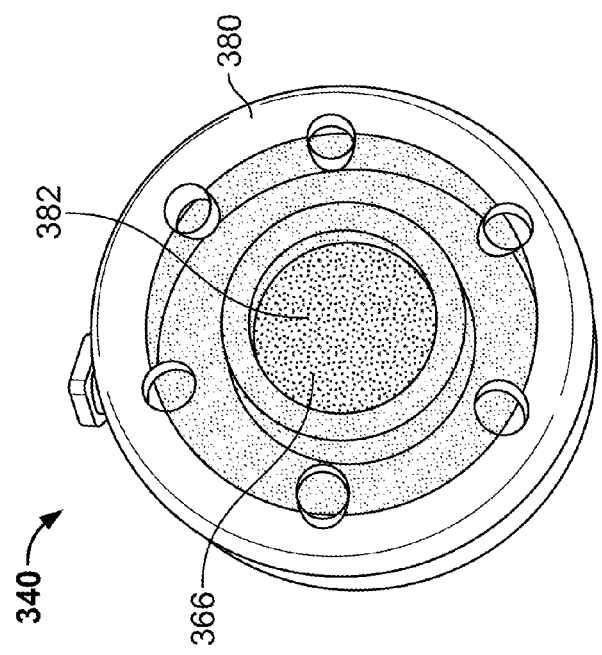
FIG. 3B is a front plan view of the transapical introducer of FIG. 3A.
Figure 3F:
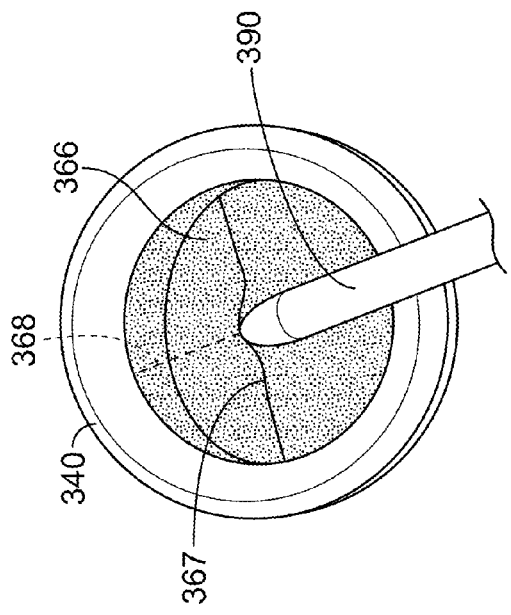
FIGS. 3F-3I show multiple views of an obturator passing through the foam seal of FIGS. 3C-E.
Figure 3G:
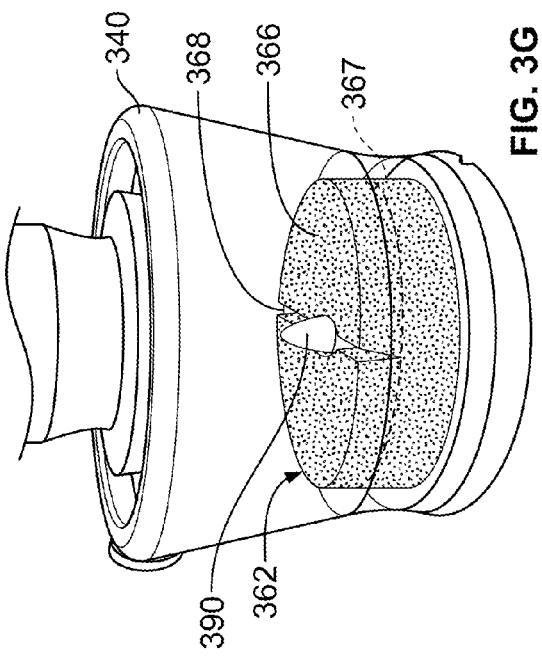

Now referring to FIGS. 3A-B, a further embodiment of a transapical introducer 300 is illustrated. The introducer 300 generally includes a hollow distal tube 310 connected to a hollow proximal tube 330 by a connector 320. These elements are substantially similar to the distal tubes 110, 210, the proximal tubes 130, 230, and connectors 120, 220 described in relation to the introducers 100 and 200 above. Connected to the proximal tube 330 is a housing 340. The housing 340 is similar to the housings 140, 240 described in relation to the introducers 100, 200, although the housing 340 may be differently shaped to appropriately house components contained therein. The components in the housing 340 may include, for example, a flush port 350, a foam seal 366 abutting a shoulder 341 in the housing, and a housing cap 380. The shoulder 341 may take the form of an annulus, with a first side of the foam seal 366 abutting the shoulder and a second side of the foam seal abutting the housing cap 380.

The flush port 350, which is distal to the housing cap 380, the foam seal 366, and the shoulder 341, may be similar or identical in structure and function as the flush ports 150, 250 described in relation to the transapical introducers 100, 200, respectively. Similarly, the housing cap 380, at the proximal most end of the housing 340, may be similar or identical in structure and function to the housing caps 180, 280 described in relation to the transapical introducers 100, 200, having a chamfered surface leading to a central opening 382.

Figure 3E:
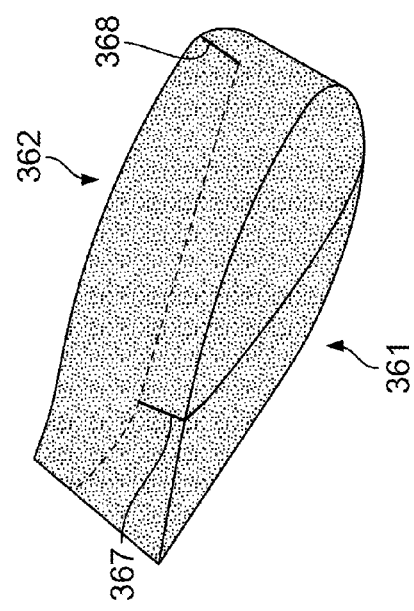
Figure 3H:
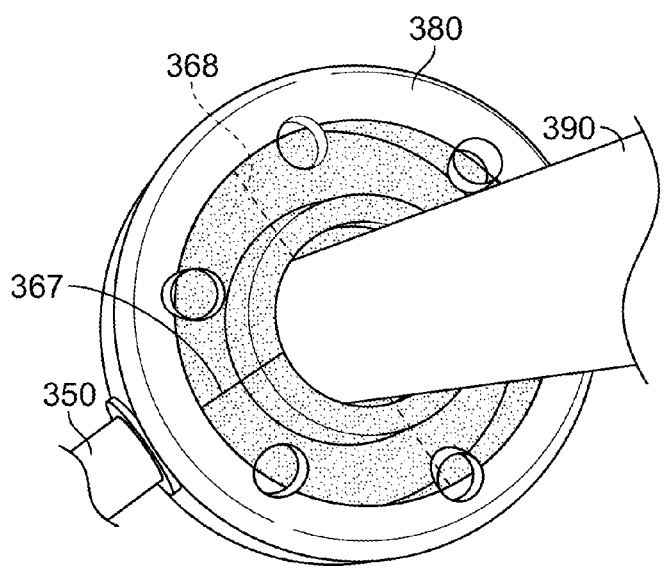

The foam seal 366 is illustrated in more detail in FIGS. 3C-J. In the illustrated embodiment, and as best seen in FIGS. 3C-E, the foam seal 366 takes the form of a short cylinder flanked by the housing shoulder 341 and the housing cap 380, as shown in FIG. 3A. A first slit 367 is formed across a first surface 361 of the foam seal 366, the first slit extending across a center area of the first surface, which may be along a diameter of the foam seal. The first slit 367 extends approximately half the thickness of the foam seal 366. A second slit 368 is formed across a second surface 362 of the foam seal 366, the second slit extending across a center area of the second surface, which may be along a diameter of the foam seal. The second slit 368 also extends approximately half the thickness of the foam seal 366. Neither the first slit 367 nor the second slit 368 need extend completely across a complete diameter of their respective surfaces 361, 362, but this configuration may be the easiest to produce. For example, the slits 367, 368 may not extend to the outer edge of the respective surfaces 361, 362, on one or both sides of the slits.

The first slit 367 may be generally perpendicular to the second slit 368. Note that in certain of FIGS. 3B-3J, the first slit 367 or second slit 368 may be represented in phantom lines when the particular slit would not otherwise be visible. With this generally perpendicular configuration, the first slit 367 meets the second slit 368 at approximately the center of the foam seal 366, creating a passageway therethrough. Although the slits 367, 368 are each described as extending across the center of the respective surfaces 361, 362 of the foam seal 366 and approximately half the thickness of the foam seal, variations are possible. For example, one or both slits 367, 368 may be off-center and they need not be perpendicular to each other. Similarly, one or both of the slits 367, 368 may extend more than half the thickness of the foam seal 366. Alternately, one of the slits 367, 368 may extend less than half the thickness of the foam seal 366 if the other one of the slits 367, 367 extends more than half the thickness of the foam seal 366. However, the first slit 367 and second slit 368 should overlap to at least some degree to allow for passage of a device through the foam seal 366. In one example, the foam seal 366 has a thickness of between approximately 0.125 and 0.25 inches (3.175 to 6.35 mm). Various materials, such as silicone or urethane open-cell foam may be used for the foam seal 366.

Figure 3I:
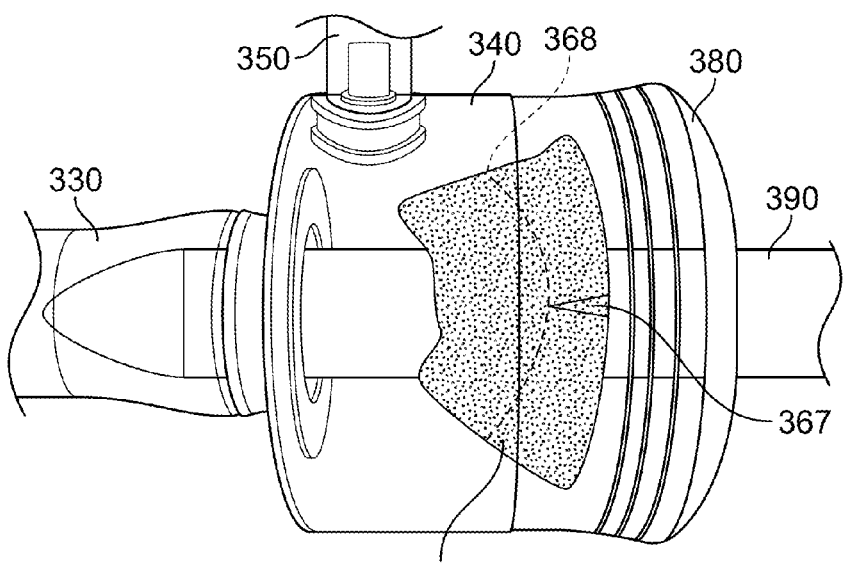
Figure 3J:
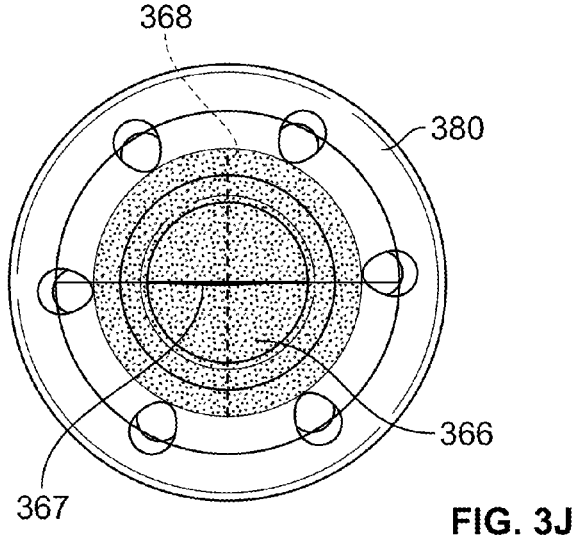
FIG. 3J shows a front plan view of the transapical introducer of FIG. 3A after an obturator has been withdrawn.

As a device, such as an obturator 390, is passed through the foam seal 366, as illustrated in FIGS. 3F-3I, the device first passes through the first slit 367 and then through the second slit 368. To properly pass through both slits 367, 368, the device should be inserted through the point at which the slits intersect to form a passageway. The foam seal 366, having an amount of elasticity, conforms around the device to create and maintain a fluid seal while the device passes through the foam seal (see FIG. 3I). After the device is removed from the foam seal 366, as illustrated in FIG. 3J, the foam seal, including first slit 367 and second slit 368, self-close, maintaining a fluid seal across the foam seal.

As the device passes through the foam seal 366, axial or rotational friction may be created. Axial friction, causing the foam seal 366 to be pulled somewhat in the direction of movement of the device, is best illustrated in FIG. 3I. This movement may be at least partially resisted by the housing shoulder 341 abutting the foam seal 366, as described above in relation to FIG. 3A. It is noted that FIGS. 3B and 3F-J omit elements within the housing 340 (including the shoulder 341) other than the foam seal 366 for clarity of illustration. The amount of friction created depends on a number of factors, including the size of the device, the material of the foam seal 366 and the material of the particular device passing through the foam seal. For example, if silicone foam is used for the foam seal 366, it may be advantageous to use silicone lubricant oil on the foam seal to minimize friction resulting from normal use.

FIG. 3K illustrates a modified embodiment of an introducer 300' that is similar to the introducer 300 in most regards. However, the introducer 300' includes an added retaining element feature in the housing 340' to help further restrict the foam seal 366 from axial or rotational movement caused by friction. The particular retaining element illustrated is a series of spikes 342' extending radially inward from the housing 340'. One, two, or more spikes 342' may be used with the housing, generally arranged circumferentially around the housing 340' and equally spaced, although variations in spacing and number of such retaining elements is possible.

Figure 4C:
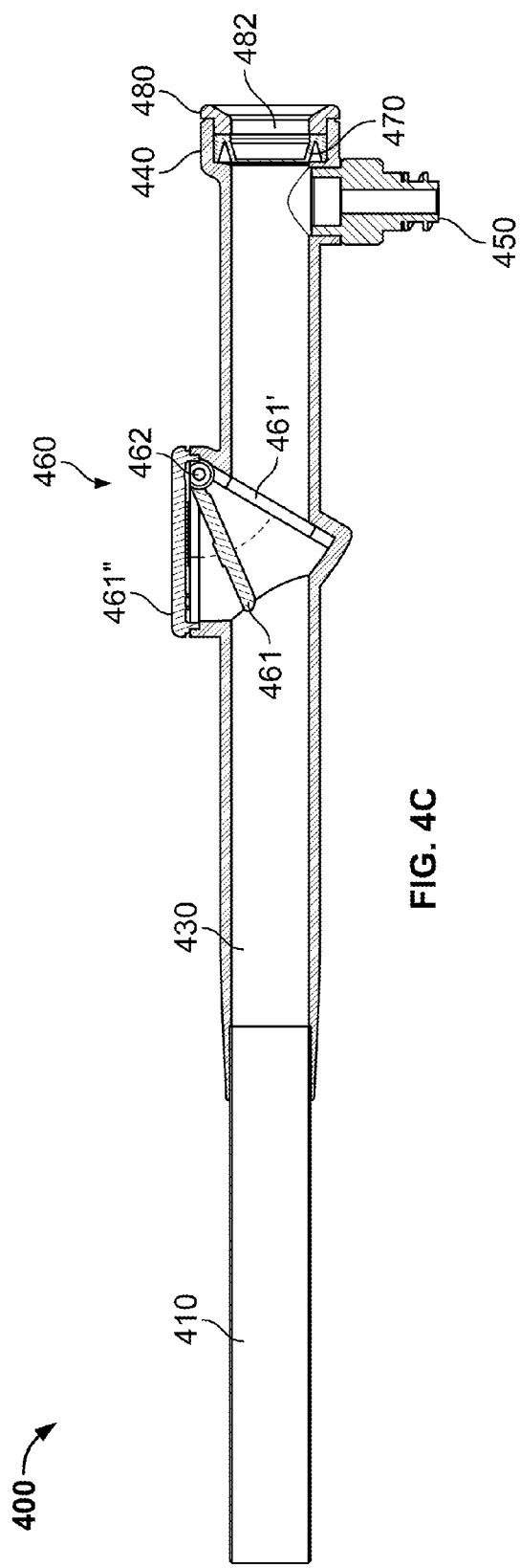
FIG. 4C is a cross sectional view of the transapical introducer of FIG. 4B taken along the line 4C-4C.

Now referring to FIGS. 4A-C, various views of a further embodiment of a transapical introducer 400 are illustrated. The introducer 400 generally includes a hollow distal tube 410 connected to a hollow proximal tube 430. The distal tube 410 may be directly connected to the proximal tube 430 as illustrated. The distal tube 410 and proximal tube 430 may alternately be formed as a single elongate tube. Connected to the proximal tube 430 is a housing 440. The housing 440 may include a number of additional components, including, for example, a wiper seal 470, and a housing cap 480. The housing cap 480 may be positioned on the proximal end of the housing 440 and include a chamfered surface leading to a central aperture 482, similar to the housing caps 180, 280, 380 described in relation to the transapical introducers 100, 200, 300, respectively. The wiper seal 470 may be positioned distal to the housing cap 480 and proximal to a flush port 450, the wiper seal being similar or identical to the wiper seals 170, 270 described above in relation to the transapical introducers 100, 200, respectively. The flush port 450 may be included in the proximal tube 430 distal of the housing 440. The flush port 450 may be identical to the flush ports 150, 250, 350 described in relation to the transapical introducers 100, 200, 300, respectively.

Similar to the distal tubes 110, 210, 310 described in relation to the transapical introducers 100, 200, 300, respectively, the distal tube 410 may be formed of a rigid material to provide radial strength during apex introduction and also during insertion of devices through the distal tube. Unlike the proximal tubes 130, 230, 330, however, the proximal tube 430 may also be formed of a rigid and translucent material.

The proximal tube 430 may also include a valve housing 460. As best illustrated in FIG. 4C, the valve housing 460 may include a pivotable or hinged flap or valve, such as a drop-leaf valve 461, hingedly connected to the valve housing by, for example, a pin 462. The drop-leaf valve 461 may take different shapes, such as the general "U" shape illustrated, but should be large enough to be capable of fluidly sealing the introducer 400. The drop-leaf valve 461 includes a biasing mechanism to bias the drop-leaf valve to a closed position 461'. The biasing mechanism may be, for example, a spring mechanism in the pin 462.

Figure 4D:
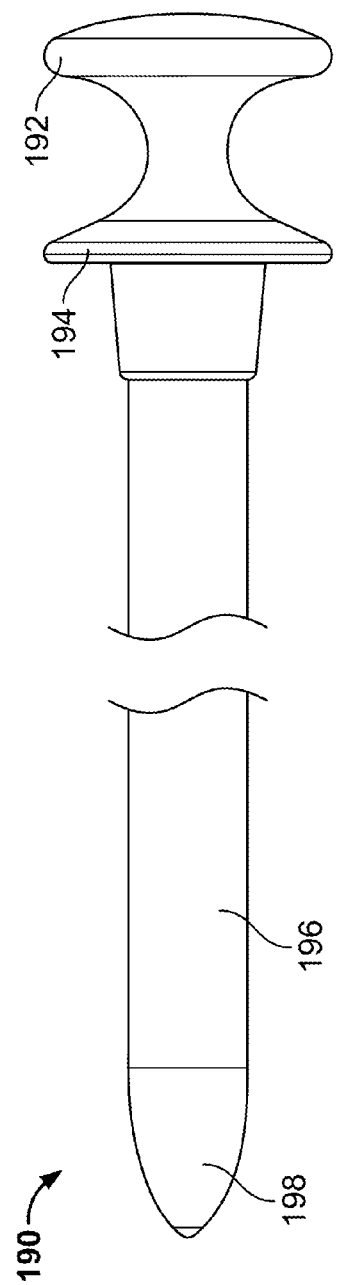
FIG. 4D is a side plan view of an obturator.

In practice, the introducer 400 is used similarly to the embodiments described above. An obturator 190, illustrated in FIG. 4D (which may be identical to the obturators 190, 390 illustrated in FIGS. 1D, 3I respectively), is advanced through the central opening 482 of the housing cap 480 and further through the wiper seal 470 prior to inserting the introducer 400 into the heart. Initially, the drop-leaf valve 461 is biased shut in the closed position 461'. As the tip 198 of the obturator 190 makes contact with the drop-leaf valve 461, it pushes the drop-leaf valve 461 toward the open position 461". Although the flush port 450 is positioned distal to the housing 440 rather than within the housing as shown in other embodiments, once the obturator 461 is inside the introducer 400, the user may flush the introducer to remove air trapped therein as described with previous embodiments.

After flushing, the introducer 400 is inserted into the heart far enough that a portion of the distal tube 410 crosses the heart tissue, with the entire proximal tube 430, including the valve housing 460 and the housing 440 remaining outside of the heart. The introducer 400 may be inserted into the heart at an angle, such that the proximal end of the introducer 400 is higher than the distal end of the introducer. In this position, air bubbles trapped in the introducer tend to move away from the heart.

Once the introducer 400 is at the desired position in the heart, the obturator 190 is slowly withdrawn from the introducer. Because the obturator 190 is sized to fill most or all of the space within the distal tube 410 and proximal tube 430, withdrawal of the obturator creates a pressure gradient causing blood to flow from the heart into the introducer 400. As the tip 198 of the obturator 190 moves proximally past the drop-leaf valve 461, the biasing force on the drop-leaf valve causes the drop-leaf valve to move from the open position 461" to the closed position 461'. After the obturator 190 is fully removed, the distal tube 410 and the portion of the proximal tube 430 distal to the drop-leaf valve should be filled with blood In the embodiment illustrated in FIGS. 4A-C, the valve housing 460 is somewhat larger than the size of the proximal tube 430. This increased size is useful to allow the drop-leaf valve 461 to move through its full range of motion while still allowing a device, such as the obturator 190, to substantially or completely occupy the diameter of the proximal tube 430. This sizing results in the potential for air bubbles to be trapped as the obturator 190 is being removed proximally across the valve housing 461, particularly if any air is trapped between the drop-leaf valve 461 and the top of the valve housing 460 when the drop-leaf valve is in the open position 461". To minimize the possibility of trapping air bubbles, the obturator 190 should be removed slowly from the introducer 400. Additionally, the tapered tip 198 of the obturator may help reduce the likelihood of air becoming trapped just distally of the drop-leaf valve 461. As the obturator 190 is removed, the drop-leaf valve 461 gently rides along the surface of the tapered tip 198 of the obturator as the drop-leaf valve moves to the closed position 461'. The configuration of the valve housing 461 and drop-leaf valve 461 eliminates the need to clamp the proximal tube 430 after removal of the obturator 190.

The user may inspect the inside of the proximal tube 430, as it is translucent, to check if air bubbles remain in the proximal tube. If the user is satisfied, he may fully remove the obturator 190 from the introducer 400 and begin the treatment procedure.

Generally, the same procedures may be performed using the introducer 400 as with other embodiments of introducers described above. Depending on the specific procedure, as well as the configuration of the obturator 190, it may be advantageous for the valve housing 460 to be located more proximally on the proximal tube 430 than shown. This is because it is desirable for a device to occupy the full diameter of the wiper seal 470 prior to the distal end of the device causing the drop-leaf valve to begin opening. For example, some devices used in procedures compatible with the introducer 400 may have a working tip at the distal end of the device with a smaller diameter than the cylindrical shaft of the device. If the working tip were to start to open the drop-leaf valve 461 prior to the shaft of the device occupying the full diameter of the wiper seal 470, the drop-leaf valve could open before the wiper seal established a fluid seal.

Although the disclosure herein has been described with reference to particular embodiments, it is to be understood that these embodiments are merely illustrative of the principles and applications of the present disclosure. It is therefore to be understood that numerous modifications may be made to the illustrative embodiments and that other arrangements may be devised without departing from the spirit and scope of the present disclosure as defined by the appended claims. It will be appreciated that the various dependent claims and the features set forth therein can be combined in different ways than presented in the initial claims. It will also be appreciated that the features described in connection with individual embodiments may be shared with others of the described embodiments The following Paragraphs summarize certain aspects of the disclosure.

Paragraph A: An introducer comprises a housing near a proximal end of the introducer, a first valve in the housing, a flexible proximal tube coupled to the housing, and a rigid distal tube coupled to a distal end of the proximal tube, wherein the proximal tube is more flexible than the distal tube and is capable of being clamped to prevent fluid flow therethrough.

Paragraph B: The introducer of Paragraph A, wherein the proximal tube is translucent.

Paragraph C: The introducer of Paragraph A, wherein the first valve is a duckbill valve.

Paragraph D: The introducer of Paragraph C, further comprising a wiper seal in the housing disposed proximally of the duckbill valve.

Paragraph E: The introducer of Paragraph D, further comprising a second valve in the housing.

Paragraph F: The introducer of Paragraph E, wherein the second valve is a duckbill valve.

Paragraph G: The introducer of Paragraph F, wherein the first duckbill valve is oriented to allow fluid to flow across the first duckbill valve only in a first direction and the second duckbill valve is oriented to allow fluid to flow across the second duckbill valve only in a second direction, the first direction being opposite the second direction.

Paragraph H: The introducer of Paragraph A, wherein the proximal tube is formed of a material selected from the group consisting of polytetrafluoroethylene, polyfluoroethylene, polyurethane, and polyethylene.

Paragraph I: The introducer of Paragraph A, wherein the distal tube is formed of a material selected from the group consisting of stainless steel, carbon reinforced nylon, and composite wound tubing.

Paragraph J: The introducer of Paragraph A, wherein the distal tube is formed of a material with am odulus of elasticity greater than about 10 GPa.

Paragraph K: The introducer of Paragraph J, wherein the modulus of elasticity of the material forming the distal tube is greater than about 40 GPa.

Paragraph L: The introducer of Paragraph K, wherein the modulus of elasticity of the material forming the distal tube is greater than about 100 GPa.

Paragraph M: The introducer of Paragraph L, wherein the modulus of elasticity of the material forming the distal tube is greater than about 190 GPa.

Paragraph N: The introducer of Paragraph A, wherein the proximal tube is formed of a material with a modulus of elasticity between about 0.35 GPa and about 1.75 GPa.

Paragraph O: The introducer of Paragraph N, wherein the modulus of elasticity of the material forming the proximal tube is between about 0.5 GPa and about 1 GPa.

Paragraph P: An introducer comprises a housing near a proximal end of the introducer, a foam seal located in the housing, a flexible proximal tube coupled to the housing, and a rigid distal tube coupled to a distal end of the proximal tube, wherein the proximal tube is more flexible than the distal tube and is capable of being clamped to prevent fluid flow therethrough.

Paragraph Q: The introducer of Paragraph P, wherein the proximal tube is translucent.

Paragraph R: The introducer of Paragraph P, wherein the foam seal includes a first slit on a first surface of the foam seal and a second slit on a second surface of the foam seal, the first surface being opposite the second surface and the first slit being generally perpendicular to the second slit.

Paragraph S: The introducer of Paragraph P, wherein the housing further comprises a shoulder and a housing cap, the foam seal being positioned between the shoulder and the housing cap.

Paragraph T: The introducer of Paragraph S, wherein the housing further comprises at least one foam seal retaining element.

Paragraph U: The introducer of Paragraph T, wherein the at least one foam seal retaining element is a spike extending radially inward from the housing.

Paragraph V: The introducer of Paragraph S, wherein the housing further comprises a plurality of spikes spaced circumferentially around an inside of the housing, each of the plurality of spikes extending radially inward from the housing.

Paragraph W: The introducer of Paragraph P, wherein the proximal tube is formed of a material selected from the group consisting of polytetrafluoroethylene, polyfluoroethylene, polyurethane, and polyethylene.

Paragraph X: The introducer of Paragraph P, wherein the distal tube is formed of a material selected from the group consisting of stainless steel, carbon reinforced nylon, and composite wound tubing.

Paragraph Y: The introducer of Paragraph P, wherein the distal tube is formed of a material with a modulus of elasticity greater than about 10 GPa.

Paragraph Z: The introducer of Paragraph Y, wherein the modulus of elasticity of the material forming the distal tube is greater than about 40 GPa.

Paragraph AA: The introducer of Paragraph Z, wherein the modulus of elasticity of the material forming the distal tube is greater than about 100 GPa.

Paragraph BB: The introducer of Paragraph AA, wherein the modulus of elasticity of the material forming the distal tube is greater than about 190 GPa.

Paragraph CC: The introducer of Paragraph P, wherein the proximal tube is formed of a material with a modulus of elasticity between about 0.35 GPa and about 1.75 GPa.

Paragraph DD: The introducer of Paragraph CC, wherein the modulus of elasticity of the material forming the proximal tube is between about 0.5 GPa and about 1 GPa.

Paragraph EE: An introducer comprises an introducer housing near a proximal end of the introducer, a first tube coupled to the introducer housing, a valve housing on the first tube, and a flap hingedly connected to the valve housing, the flap having a first closed position and a second open position, wherein, when in the first closed position, a proximal end of the first tube is fluidly sealed from a distal end of the first tube and, when in the second open position, the proximal end of the first tube is in fluid communication with the distal end of the first tube.

Paragraph FF: The introducer of Paragraph EE, wherein the flap is connected to the valve housing by a pin.

Paragraph GG: The introducer of Paragraph EE, wherein a biasing mechanism biases the flap toward the first closed position.

Paragraph HH: The introducer of Paragraph GG, wherein the biasing mechanism comprises a spring.

Paragraph II: The introducer of Paragraph EE, further comprising a second tube coupled to a distal portion of the first tube.

Paragraph JJ: The introducer of Paragraph II, wherein the first tube is translucent.

The invention claimed is:

1. An introducer comprising:
 a housing near a proximal end of the introducer;
 a first valve in the housing;
 a second valve in the housing;
 a flexible proximal tube coupled to the housing; and
 a rigid distal tube coupled to a distal end of the proximal tube;
 wherein the proximal tube is more flexible than the distal tube and is capable of being clamped to prevent fluid flow therethrough,
 wherein the first valve is oriented to allow fluid to flow across the first valve only in a first direction and the second valve is oriented to allow fluid to flow across the second valve only in a second direction, the first direction being opposite the second direction.

2. The introducer of claim 1, wherein the proximal tube is translucent.

3. The introducer of claim 1, wherein the first valve is a duckbill valve.

4. The introducer of claim 3, further comprising a wiper seal in the housing disposed proximally of the first valve.

5. The introducer of claim 1, wherein the second valve is a duckbill valve.

6. The introducer of claim 1, wherein the proximal tube is formed of a material selected from the group consisting of polytetrafluoroethylene, polyfluoroethylene, polyurethane, and polyethylene.

7. The introducer of claim 1, wherein the distal tube is formed of a material selected from the group consisting of stainless steel, carbon reinforced nylon, and composite wound tubing.

8. The introducer of claim 1, wherein the distal tube is formed of a material with a modulus of elasticity greater than about 10 GPa.

9. The introducer of claim 8, wherein the modulus of elasticity of the material forming the distal tube is greater than about 40 GPa.

10. The introducer of claim 9, wherein the modulus of elasticity of the material forming the distal tube is greater than about 100 GPa.

11. The introducer of claim 10, wherein the modulus of elasticity of the material forming the distal tube is greater than about 190 GPa.

12. The introducer of claim 1, wherein the proximal tube is formed of a material with a modulus of elasticity between about 0.35 GPa and about 1.75 GPa.

13. The introducer of claim 12, wherein the modulus of elasticity of the material forming the proximal tube is between about 0.5 GPa and about 1 GPa.

* * * * *